United States Patent [19]

Bires et al.

[11] Patent Number: 5,252,325
[45] Date of Patent: * Oct. 12, 1993

[54] CONDITIONING HAIR CARE COMPOSITIONS

[75] Inventors: Carmen D. Bires, Hackettstown; Stephen L. Kopolow, Plainsboro; William J. Burlant, Wayne; Michael W. Helioff, Westfield; Robert B. Login, Oakland, all of N.J.; Mohammed Tazi, Marietta, Ga.

[73] Assignee: ISP Investments Inc., Wilmington, Del.

[*] Notice: The portion of the term of this patent subsequent to Dec. 17, 2008 has been disclaimed.

[21] Appl. No.: 857,150

[22] Filed: Mar. 25, 1992

Related U.S. Application Data

[63] Continuation-in-part of Ser. No. 638,597, Jan. 8, 1991, Pat. No. 5,169,622, and a continuation-in-part of Ser. No. 638,598, Jan. 8, 1991, Pat. No. 5,169,623.

[51] Int. Cl.$^5$ .......................... A61K 7/11; A61K 7/06
[52] U.S. Cl. ......................................... 424/71; 424/70; 424/401; 252/304; 525/283
[58] Field of Search .............. 424/71, 70, 401; 525/283; 252/304

[56] References Cited

U.S. PATENT DOCUMENTS

| | | | |
|---|---|---|---|
| 4,366,099 | 12/1982 | Gáetani et al. | 525/283 |
| 4,902,499 | 2/1990 | Bolish, Jr. et al. | 424/71 |
| 4,923,694 | 5/1990 | Shih et al. | 424/70 |
| 5,073,296 | 12/1991 | Kopolow et al. | 424/401 |
| 5,077,040 | 12/1991 | Bergmann et al. | 424/70 |

Primary Examiner—Thurman K. Page
Assistant Examiner—Sally Gardner
Attorney, Agent, or Firm—Walter Katz; Marilyn J. Maue; Joshua J. Ward

[57] ABSTRACT

What is provided herein are conditioning hair care compositions comprising (a) a stabilized silicone product obtained by in situ polymerization of a water-soluble vinyl monomer, preferably vinylpyrrolidone, in the presence of discrete microdroplets of a silicone oil in water, (b) an emulsifiers, (c) a thickener, optionally, (d) a cationic surfactant, and the balance being (e) water.

8 Claims, No Drawings

CONDITIONING HAIR CARE COMPOSITIONS

CROSS-REFERENCE TO RELATED PATENT APPLICATIONS

This application is a continuation-in-part of copending U.S. patent applications Ser. No. 638,597, now U.S. Pat. No. 5,169,622, filed Jan. 8, 1991, and Ser. No. 638,598, filed Jan 8, 1991, now U.S. Pat. No. 5,169,623.

BACKGROUND OF THE INVENTION

1. Field of the Invention

This invention relates to hair care compositions, and more particularly, to silicone-containing conditioning formulations.

2. Description of the Prior Art

Conditioning hair care compositions in the form of shampoos and mousses are commercial formulations for personal hair care use. Conditioning compositions usually require a fixative resin as the active material to condition the hair. See, for example, U.S. Pat. Nos. 4,897,262, 3,862,306, 4,567,035, 4,315,910, 4,164,562, 4,923,695, 5,066,481, 4,923,694, 4,521,404 and 4,223,009.

The use of silicones in conditioning shampoos also is known in the art. See, for example, U.S. Pat. Nos. 3,957,970; 4,472,375; 4,559,227; 4,586,518; 4,728,457; 4,741,855; 4,749,565; 4,749,732; 4,788,006; and 4,849,127. However, these and other patents and publications have not provided entirely satisfactory stable dispersions of silicones in an aqueous formulation, and/or an effective hair conditioning product.

Accordingly, it is an object of the invention to provide a conditioning hair care composition which contains silicone in stable, dispersed form.

Another object of this invention is to provide a silicone-containing conditioning composition which has advantageous properties for the user.

Still another object is to provide a homogeneous silicone-containing conditioner which can be formulated by a simple process.

These and other objects and features of the invention will be made apparent by the following description of the invention herein.

Unless otherwise indicated, all percentages and ratios herein are by weight.

SUMMARY OF THE INVENTION

What is provided herein are conditioning hair care compositions comprising (a) a stabilized silicone product obtained by in situ polymerization of a water-soluble vinyl monomer, preferably vinylpyrrolidone, in the presence of discrete microdroplets of a silicone oil in water, (b) an emulsifier, (c) a thickener, optionally, (d) a cationic surfactant, and the balance being (e) water.

DETAILED DESCRIPTION OF THE INVENTION

The essential as well as optional components are described below.

Essential Components

(a) Stabilized Silicone Product

The active material to be dispersed in an aqueous medium are silicone oils which are water-insoluble liquids at room temperature, and are cosmetically-active, i.e. they impart hair conditioning and style retention properties to hair care formulations.

Suitable silicone oils or fluids for use in the invention are selected from non-volatile polyalkyl siloxanes, polyaryl siloxanes, polyalkylaryl siloxanes and polyether siloxane copolymers. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5–600,000 centistokes (cs) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cs, and most preferably, a viscosity of up to about 15,000 cs.

Suitable non-volatile polyalkylarylsiloxanes include, for example, polymethylphenylsiloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

In the practice of the present invention, the silicone oil to be dispersed is first added to water and then subjected to agitation to produce a fine dispersion of discrete silicone oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Thereafter, a water-soluble vinyl monomer, for example, a vinylpyrrolidone monomer such as vinylpyrrolidone itself or a derivative thereof such as an alkyl vinyl pyrrolidone, and, optionally, a water soluble acryl comonomer, such as methacrylamidopropyl trimethylammonium chloride (MAPTAC), is added to the mixture, along with an appropriate free radical polymerization initiator.

Suitable free radical polymerization initiators for polymerization of water-soluble vinyl monomers include such free radical catalysts as t-butylperoctoate, t-butylperoxy- pivalate and the like. Oil-soluble catalysts are preferred.

Thereafter, the reaction mixture is maintained at a temperature in the range of about 55° to 85° C., preferably, about 75° to 85° C., and most preferably, about 78° to 82° C., for a period of time sufficient to effect the desired polymerization and form the aqueous polymer solution necessary to stabilize the discrete microdroplets of the silicone oil.

As the polymerization proceeds, the dispersed silicone microdroplets become white and appear to precipitate in the aqueous medium, however, without coalescing. Generally, the observance of this white or milky color in the aqueous medium is an indication of completion of the process, which usually takes about 2 to 20 hours, preferably about 4 to 10 hours, and most preferably, about 6 to 8 hours. After completion of polymerization, the residual vinyl monomer content generally is less than about 0.1%, as measured by the iodine titration method.

The production of stable, discrete microdroplets of silicone oil in the resulting aqueous polymer solution can be controlled by the viscosity of the aqueous polymer solution. For example, the viscosity of this medium can be increased by increasing the relative amount of vinyl monomer to oil in the original reaction mixture. By increasing the viscosity of the polymer solution, the proclivity to form a stable, homogeneous suspension of discrete microdroplets of oil throughout the entire medium is enhanced. On the other hand, reducing the viscosity of the medium by decreasing the amount of vinyl monomer in the initial mixture results in a more dilute concentration of polyvinyl polymer in the resultant mixture, which enhances the tendency to form a separate layer of discrete oil droplets.

Suitably, the ratio of vinyl monomer to silicone oil used in the polymerization should be in the range of about 95/5 to 5/95, respectively, on a weight basis, preferably at least about 50/50. Most preferred is a range of about 90/10 to 70/30. As used herein, a "stable composition or suspension" means that the discrete oil microdroplets remain suspended in the aqueous polymer solution for at least seven days at ambient temperature.

The viscosity of the stabilized silicone oil in water product, which is obtained by in situ polymerization of vinylpyrrolidone monomer, optionally with the acryl comonomer, suitably is in the range of about 3,000 to 100,000 cps, preferably about 4,000 to 60,000 cps, and most preferably, about 6,000 to 25,000 cps.

The diameter of the silicone microdroplets obtained are observed to be in the range of about 0.1 to 450 microns, and usually are about 1 to 100 microns.

The stabilized silicone product (20% active) suitably is present in an amount of about 0.25-25%, preferably 1-10%, and optimally about 2.5%.

(b) Emulsifier

This component is an emulsifying wax, such as glycerol stearate.

(c) Thickener

Suitable thickeners include dimethicone copolyols, guar gum, methyl cellulose starches and starch derivatives, fatty alcohols such as cetearyl alcohol and stearyl alcohol.

(d) Optional Cationic Surfactants

The cationic surfactants useful in the conditioning hair care compositions of this invention can be present at a level up to about 10%, preferably from about 2% to about 5% of the composition, and optimally about 3% (100% basis).

Cationic surfactants useful in the present conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: McCutcheon's, Emulsifiers & Detergents, (1989, published by the M. C. Publishing Company) Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

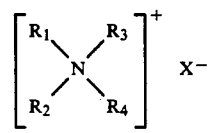

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

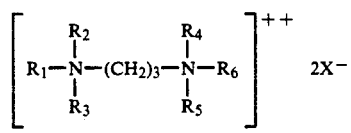

wherein $R_1$ is an aliphatic group having from about 16 to about 22 carbon atoms, $R_2$, $R_3$, $R_4$, $R_5$ and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium slats include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E. O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

(e) Water

Water is the last essential component of the present invention's compositions and generally comprises from about 70% to about 98% of the total composition.

Other Optional Components

The present compositions herein can contain a variety of other optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; sodium chloride, sodium sulfate, polyvinyl alcohol, and ethyl alcohol; pH adjusting agents such as citric acid, lactic acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts; hair reducing agents such as the thioglycolates; perfumes; and, sequestering agents such as disodium/tetrasodium ethylenediamine tetraacetate, polymer plasticizing agents such as glycerin and propylene glycol. Such agents generally are used individually at a level of from about 0.01% to about 10%, preferably from about 0.05% to about 5.0% by weight of the composition.

The pH of the present compositions is not critical and may be in the range of from about 3.5 to about 8.0.

As with all compositions, the present compositions should not contain components which unduly interfere with the performance of the compositions.

METHOD OF MANUFACTURE

Methods of manufacture of the present compositions are described in the following examples.

The invention will now be described with references to the following more particular examples.

EXAMPLE 1

The in situ polymerization process of the invention was carried out in a 1-liter laboratory reactor equipped with an overhead stirring motor, a metal anchor agitator, a nitrogen gas inlet tube, a water condenser connected to a bubbler, a temperature probe connected to a temperature controller and associated with a heating mantle, and a dropping funnel.

The reactor first was purged with nitrogen and charged with 400 g. of distilled water and 10 g. of Dimethicone oil having a viscosity of 100 cs. The oil-water mixture then was agitated vigorously at 350 rpm under nitrogen for 30 minutes whereupon the oil was dispersed as transparent, discrete microdroplets in the aqueous medium. The dispersion then was heated to 80° C. and 0.25 g. of di-tert-butylperoctoate was added. At this point, the mixture was maintained for 30 minutes with continuous stirring whereafter 90 g. of vinylpyrrolidone and an additional 0.25 g. of di-tert-butylperoctoate was added at one time while maintaining a nitrogen flow of 15 ml/min. After about 10–15 minutes, an exotherm was observed and the temperature increased to 86° C. The transparent, spherical droplets of oil became opaque. The the temperature was reduced to 80° C. and polymerization was continued for 6–8 hours with stirring. During this period, the dispersion became milky and the droplets became completely invisible. Polymerization was considered complete when the measured residual monomer content was less than 0.1%.

The composition obtained was a stable, homogeneous dispersion of microdroplets of Dimethicone oil stabilized in an aqueous polyvinylpyrrolidone solution. Upon exerting only slight pressure on the microdroplets, the silicone oil was observed to ooze out. However, the composition was quite stable for many months at room temperature, and for an extended period at the elevated temperature of 45° to 54° C.

EXAMPLES 2-3

The procedure of Example 1 was repeated using weight ratios of 80 g. of vinylpyrrolidone to 20 g. of Dimethicone oil (Example 2), and 70 g. of vinylpyrrolidone to 30 g. of Dimethicone oil (Example 3). Similar results to Example 1 were obtained in these runs.

EXAMPLE 4

The procedure of Example 1 was followed using a weight ratio of 20 g. of vinylpyrrolidone and 80 g. of Dimethicone oil. The resultant composition was not as viscous as in Example 1. The microdroplets obtained remained in discrete form, however, without coalescence, but settled to the bottom of the solution as a separate layer.

EXAMPLE 5

The procedure of Example 1 was followed using a weight ratio of 135 g. of vinylpyrrolidone to 15 g. of Dimethicone oil in 600 ml. of water. The results were substantially the same as obtained in Example 1.

EXAMPLE 6

The procedure of Example 1 was followed using a weight ratio of 135 g. of vinylpyrrolidone to 15 g. of a Dimethicone oil having a viscosity of 1,000 cs (mol. wt. of 28,000). The mixture was agitated at 700 rpm to produce a stable dispersion of the viscous silicone oil droplets in the aqueous polymer solution.

EXAMPLE 7

A pilot plant run was carried out in a 30 gal. reactor using two wide span turbine agitators having pitched and flat blades set at 200 rpm. 10,790 g. of vinylpyrrolidone, 1205 g. of Dimethicone oil, 100 cs, 48,225 g. of water, 120 g. of di-t-butylperoctoate, and 317 g. of Germaben ® preservative were used in this run. After 6 hours, polymerization was complete and a stable, homogeneous, milky aqueous dispersion of discrete, coated silicone oil droplets was obtained which dispersion remained in discrete and suspended form throughout the composition. The composition also was stable for an extended period of time.

EXAMPLE 8

The procedure of Example 1 was followed using 102 g. of vinylpyrrolidone, 11 g. of Dimethicone, 100 cs, 36 g. of a 50% aqueous solution of methacrylamidopropyl-trimethylammonium chloride, 462 g. of water, 0.1 g. of tetrasodium pyrophosphate, and 0.60 g. of di-tert-butyl-peroctoate. A stable, homogeneous composition was obtained having a residual VP content of only 0.01%.

EXAMPLE 9

The procedure of Example 1 was followed using 90 g. of vinylpyrrolidone, 10 g. of Dimethicone oil, 100 cs, 400 g. of water and 0.75 g. of Lupersol 11. The results were similar to those obtained in Example 4.

The results of these experiments are summarized in the Tables below wherein:

| VP | Vinylpyrrolidone |
|---|---|
| PVP | Polyvinylpyrrolidone |
| Acryl | a water-soluble acrylic, acrylate, |
| Comonomer | acrylamide monomer, quaternized or unquaternized, e.g. a quaternized amino acrylamide |
| MAPTAC | Methacrylamidopropyltrimethylammonium chloride |
| DM | Polydimethylsiloxane, Dimethicone, 100 cs, Petrarch Chem. Co; 1000 cs, Dow Corning Corp. |
| TBP | Tert-butyl peroctoate, e.g. Trigonox ® 21 (AKZO Chem. Co.) |
| TBPP | t-Butylperoxy pivalate, e.g. Lupersol 11 (Atochem N.A.) |
| Brookfield Viscosity | Viscosity of stabilized oil in water product in cps, as measured using a RVT spindle # 3 @ 70 rpm |

TABLE I

| Ex. No. | Monomer | Amt (g) | Silicone Oil | Amt (g) | Viscosity (cs) | MW |
|---|---|---|---|---|---|---|
| 1 | VP | 90 | DM | 10 | 100 | 5970 |
| 2 | VP | 80 | DM | 20 | 100 | 5970 |
| 3 | VP | 70 | DM | 30 | 100 | 5970 |
| 4 | VP | 20 | DM | 80 | 100 | 5970 |
| 5 | VP | 135 | DM | 15 | 100 | 5970 |
| 6 | VP | 135 | DM | 15 | 1000 | 28,000 |
| 7* | VP | 10,790 | DM | 1205 | 100 | 5970 |
| 8 | VP | 102 | DM | 11 | 100 | 5970 |
| 9 | VP | 90 | DM | 10 | 100 | 5970 |

TABLE I-A

| Ex. No. | Co-monomer | Amt (g) | Medium | Amt (g) | Initiator | Amt (g) | Agitation (rpm) |
|---|---|---|---|---|---|---|---|
| 1 | — | — | Water | 400 | TBP | 0.75 | 350 |
| 2 | — | — | Water | 400 | TBP | 0.75 | 350 |
| 3 | — | — | Water | 400 | TBP | 0.75 | 350 |
| 4 | — | — | Water | 400 | TBP | 0.75 | 350 |
| 5 | — | — | Water | 600 | TBP | 0.76 | 350 |
| 6 | — | — | Water | 600 | TBP | 0.76 | 700 |
| 7* | — | — | Water | 48,225 | TBP | 120 | 200 |
| 8 | MAPTAC | 18 | Water | 462 | TBP | 0.60 | 350 |
| 9 | — | — | Water | 400 | TBPP | 0.75 | 350 |

*Pilot plant run

TABLE II

| Ex. No. | % Solids | Brookfield Viscosity (cps) | Diameter of Microspheres (microns) Mean | Range |
|---|---|---|---|---|
| 1 | 19.7 | 7,200 | — | — |
| 2 | 22.0 | 24,400 | | 1–14 |
| 3 | 21.1 | 17,300 | | 1–17 |
| 4 | 20.0 | — | | |
| 5 | | | | |
| 6 | 20.6 | 10,200 | 56 | |
| 7 | 20.2 | 8,900 | 80 | 3–54 |
| 8 | 30.3 | 11,300 | — | — |
| 9 | 20.2 | 7,200 | — | — |

The present compositions are used in a conventional manner.

The following Examples further illustrate the preferred embodiments within the scope of the present invention. The Examples are given solely for the purposes of illustration and are not to be construed as limitations of the present invention as many variations of the invention are possible without departing from its spirit and scope.

The following examples are representative of the conditioning shampoo hair care compositions of the present invention.

TABLE A

CONDITIONING HAIR CARE COMPOSITION

| Components | Concentration (%) by Weight | | |
|---|---|---|---|
| | Suitable | Preferred | Optimum |
| (a) Stabilized Silicone Product (of Exs 1–9, 20% active) | 0.5–10 | 1–5 | 2.5 |
| (b) Emulsifier + (c) Thickener | 1–10 | 2–7 | 3.5 |
| (d) Cationic Surfactant (100% basis) | 0–10 | 2–5 | 3.0 |
| (e) Water | qs | qs | qs |

TABLE B

PROPERTIES OF CONDITIONING COMPOSITION OF INVENTION

| | Composition | | |
|---|---|---|---|
| | Suitable | Preferred | Optimum |
| pH | 4–7.5 | 5–7 | 6 |
| Viscosity, cps | 2,000–15,000 | 3,000–8,000 | 5,000 |

The following is a specific example representative of the conditioning composition of the present invention.

TABLE C

| Ingredient | Weight % |
|---|---|
| Emulsifying wax | 3.5 |
| Stearyl alcohol + Ceteareth-20 | 1.5 |
| Glycol stearate | 0.5 |
| PVP/Silicone (90/10, Ex. 1) | 2.5 |

TABLE C-continued

| Ingredient | Weight % |
| --- | --- |
| Laneth-16 + Ceteth-16 + Oleth-16 + Steareth-16 | 0.3 |
| Methylparaben | 0.2 |
| Propylparaben | 0.1 |
| Water | qs |

In combination with the above composition, the addition of stearyl dimethylbenzyl ammonium chloride in the amount of 2–10% by weight of the composition as a cationic surfactant improves the detangling properties of the composition.

The conditioning compositions of the invention also exhibit excellent properties in actual use on hair including effective curl retention, enhanced hair stiffness, capability for mending split ends, conditioning damaged hair, builds body, and advantageous curl snap, in direct comparative testing with other related products having silicone dispersed therein.

While the invention has been described with particular reference to certain embodiments thereof, it will be understood that changes and modifications may be made which are within the skill of the art. Accordingly, it is intended to be bound only by the following claims, in which:

What is claimed is:

1. A conditioning hair care composition comprising
   (a) about 0.5–10% by weight at 20% solids of a stabilized silicone product made by in situ polymerization of a water-soluble vinyl monomer which is vinylpyrrolidone or vinylpyrrolidone copolymerized with an acryl comonomer which is methacrylamidopropyl trimethylammonium chloride in the presence of microdroplets of 0.1 to 450 microns in diameters of a non-volatile silicone oil having a viscosity between about 100 and 100,000 cs, in water, wherein the weight ratio of the vinylpyrrolidone monomer to silicone oil in the polymerization mixture is about 95:5 to 5:95, respectively, on a weight basis,
   (b) about 1–10% by weight of an emulsifying wax including glycerol stearate, and
   (c) a thickener,
   (d) up to 10% by weight of a cationic surfactant comprising a quaternary ammonium compound, and the balance being
   (e) water.

2. A conditioning hair care composition according to claim 1 wherein said microdroplets are homogeneously distributed throughout the conditioning hair care composition 3. A conditioning hair care composition according to claim 1 wherein said weight ratio is about 90:10 to about 50:50.

4. A conditioning hair care composition according to claim 1 wherein said diameter of said microdroplets is about 1 to 100 microns, and a Brookfield viscosity of the stabilized silicone product is about 4,000 to 60,000 cps.

5. A conditioning hair care composition according to claim 2 wherein said silicone oil is a non-volatile polyalkyl siloxane, a polyaryl siloxane, a polyalkylaryl siloxane or a polyether siloxane.

6. A conditioning hair care composition according to claim 1 wherein (a) is obtained as about a 20–30% active dispersion.

7. A conditioner composition according to claim 1 comprising about 1–5% by weight at 20% solids of (a), about 2–7% by weight of (b) and (c), about 2–5% by weight of (d), the balance being (e) water.

8. A conditioner composition according to claim 1 wherein said thickener is stearyl alcohol, and said cationic surfactant is stearyl dimethylbenzyl ammonium chloride.

* * * * *